US008496875B2

(12) United States Patent
Greenstein et al.

(10) Patent No.: US 8,496,875 B2
(45) Date of Patent: Jul. 30, 2013

(54) AUTOMATED SYSTEM FOR HANDLING MICROFLUIDIC DEVICES

(75) Inventors: Michael Greenstein, Los Altos, CA (US); Colin B. Kennedy, Greenbrae, CA (US); James C. Mikkelsen, Jr., Mountain View, CA (US)

(73) Assignee: Caliper Life Sciences, Inc., Hopkinton, MA (US)

( * ) Notice: Subject to any disclaimer, the term of this patent is extended or adjusted under 35 U.S.C. 154(b) by 2148 days.

(21) Appl. No.: 11/133,943

(22) Filed: May 20, 2005

(65) Prior Publication Data

US 2006/0165559 A1    Jul. 27, 2006

Related U.S. Application Data

(60) Provisional application No. 60/572,772, filed on May 21, 2004.

(51) Int. Cl.
*G01N 21/00* (2006.01)

(52) U.S. Cl.
USPC ............ 422/65; 422/63; 422/64; 422/66; 422/67; 422/68.1; 422/401; 422/404; 422/407; 422/501; 422/509

(58) Field of Classification Search
USPC ............ 422/100, 63–68.1, 401, 404, 407, 422/501, 509
See application file for complete search history.

(56) References Cited

U.S. PATENT DOCUMENTS

| | | | |
|---|---|---|---|
| 6,132,685 A * | 10/2000 | Kercso et al. | 422/104 |
| 6,306,659 B1 | 10/2001 | Parce et al. | |
| 6,372,185 B1 * | 4/2002 | Shumate et al. | 422/100 |
| 6,447,723 B1 * | 9/2002 | Schermer et al. | 422/62 |
| 6,472,218 B1 * | 10/2002 | Stylli et al. | 436/48 |
| 6,495,369 B1 * | 12/2002 | Kercso et al. | 436/47 |
| 6,498,497 B1 | 12/2002 | Chow et al. | |
| 6,556,923 B2 * | 4/2003 | Gallagher et al. | 702/23 |
| 7,105,132 B2 * | 9/2006 | Shumate et al. | 422/100 |
| 7,244,396 B2 * | 7/2007 | Chait et al. | 422/99 |
| 7,275,807 B2 * | 10/2007 | Van Tuyl | 347/46 |
| 7,316,801 B2 * | 1/2008 | Kercso et al. | 422/65 |
| 7,429,359 B2 * | 9/2008 | Reichel et al. | 422/100 |

(Continued)

FOREIGN PATENT DOCUMENTS

| | | |
|---|---|---|
| EP | 1403644 A1 | 3/2004 |
| WO | WO-00/35260 A1 | 6/2000 |
| WO | WO-00/50247 A1 | 8/2000 |

OTHER PUBLICATIONS

American National Standard Institute/Society for Biomolecular Sciences; ANSI/SBS Jan. 2004; "For Microplates—Footprint Dimensions", Secretariat, Society for Biomolecular Screening, Jan. 2006, pp. 1-8.

*Primary Examiner* — Brian R Gordon
(74) *Attorney, Agent, or Firm* — Cardinal Law Group

(57) ABSTRACT

The present invention is an automated microfluidic chip processing apparatus that includes a deck for holding at least one microfluidic chip and capable of being accessed by a liquid handling system, a fluid control system, and a detection system, wherein a chip handling device transports the chip from the deck to the fluid control system and the detection system. The present invention also includes a chip for use with an automated microfluidic chip processing apparatus, and a method for processing a microfluidic chip using such an apparatus.

11 Claims, 15 Drawing Sheets

U.S. PATENT DOCUMENTS

| | | |
|---|---|---|
| 2001/0048899 A1 | 12/2001 | Marouiss et al. |
| 2002/0012611 A1* | 1/2002 | Stylli et al. ............... 422/65 |
| 2002/0127149 A1 | 9/2002 | Dubrow et al. |
| 2002/0153055 A1* | 10/2002 | Downs et al. ............. 141/129 |
| 2003/0017085 A1 | 1/2003 | Kercso et al. |
| 2004/0028567 A1 | 2/2004 | Parce et al. |
| 2004/0033554 A1* | 2/2004 | Powers ..................... 435/29 |
| 2005/0238542 A1* | 10/2005 | Focaracci et al. ......... 422/100 |
| 2005/0271551 A1* | 12/2005 | Shumate et al. .......... 422/100 |
| 2006/0002824 A1* | 1/2006 | Chang et al. .............. 422/100 |

* cited by examiner

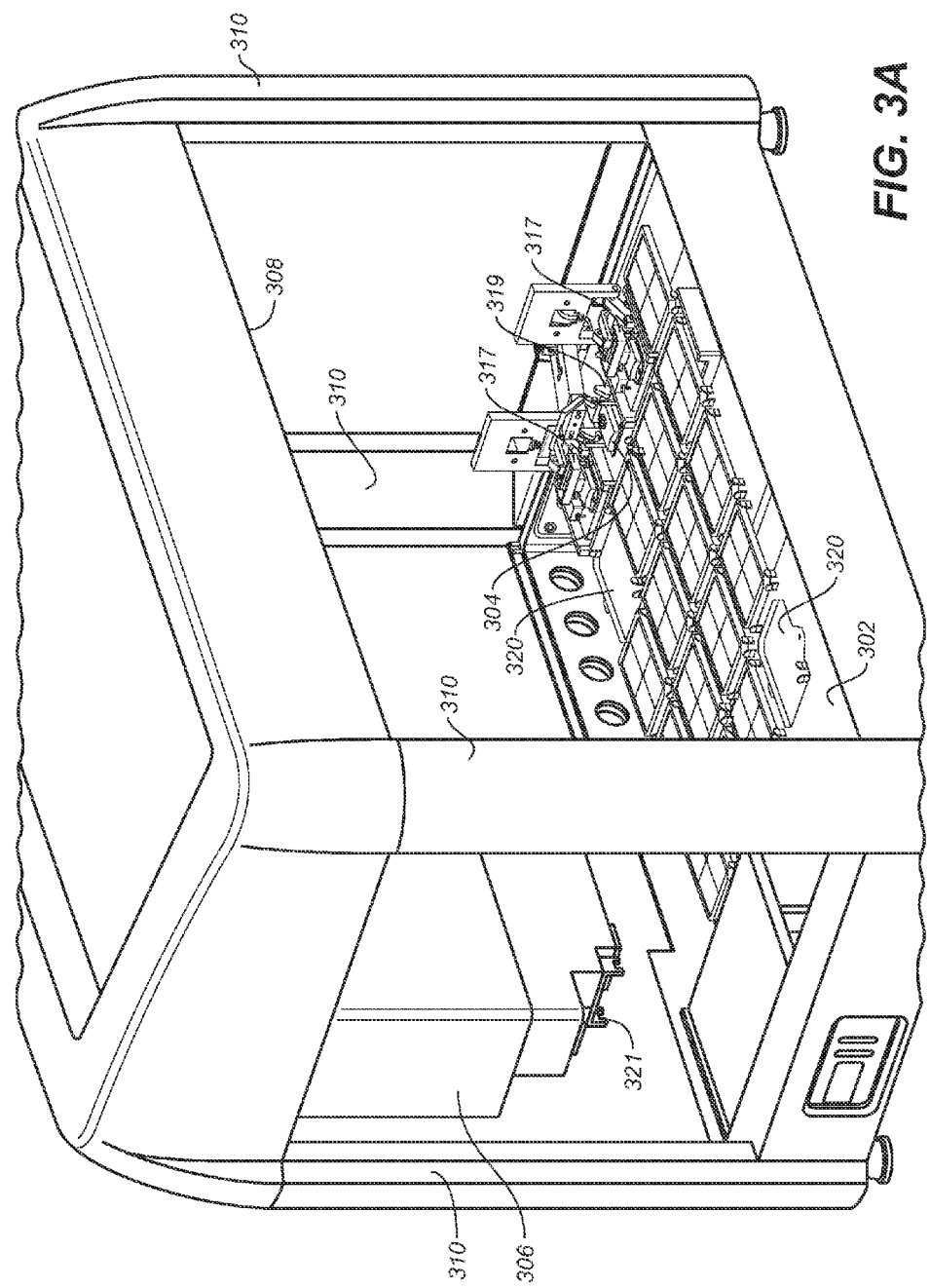

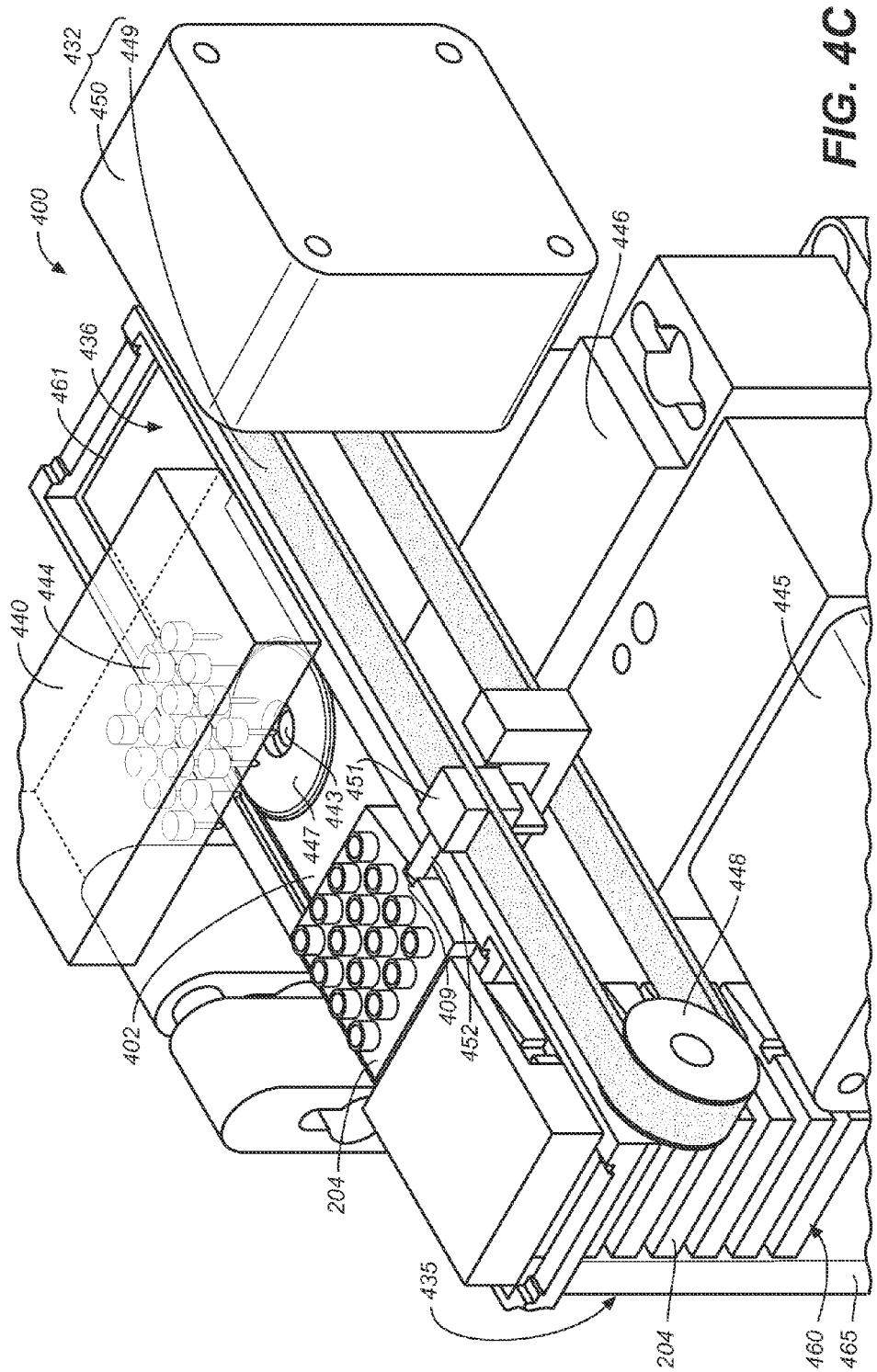

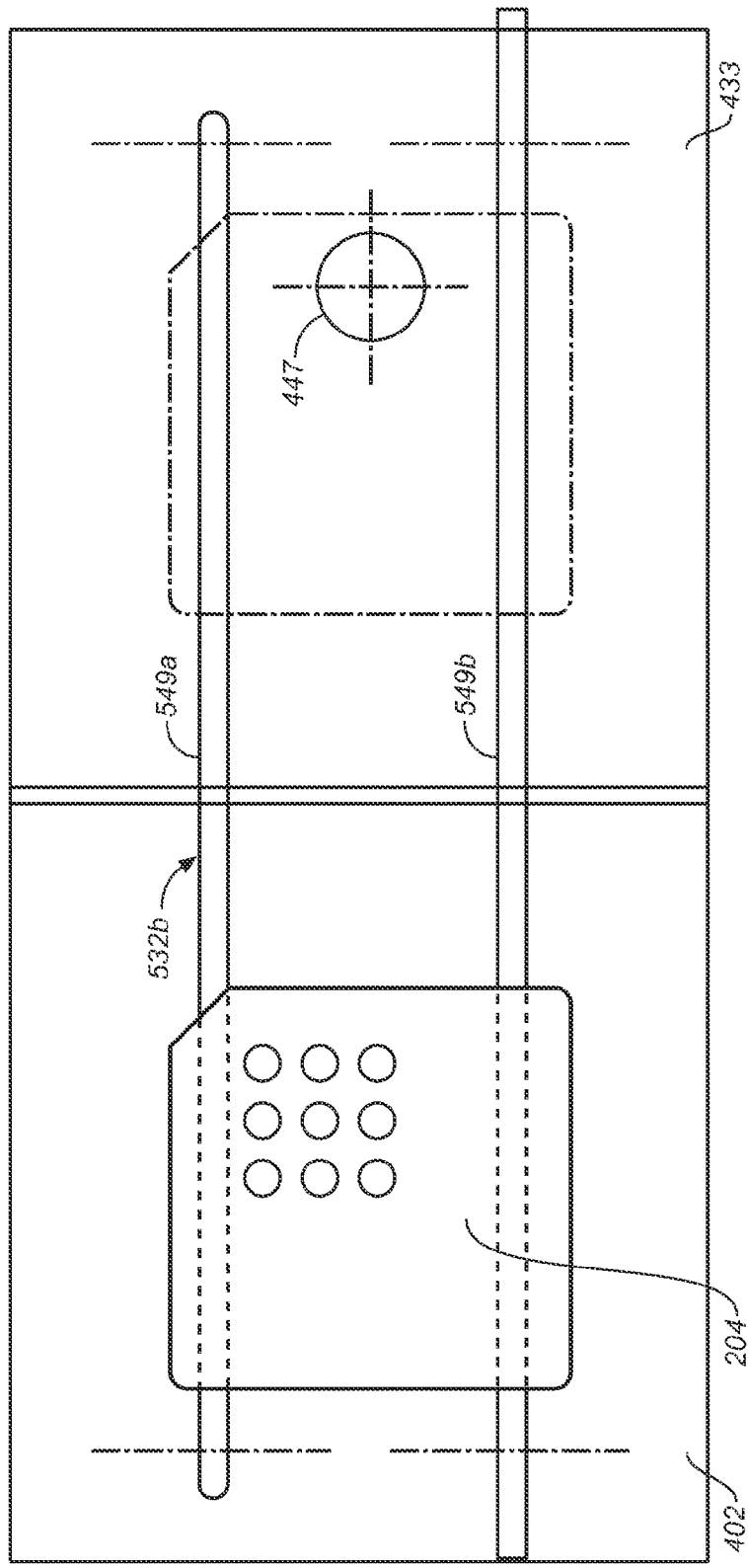

AUTOMATED SYSTEM FOR HANDLING MICROFLUIDIC DEVICES

FIELD OF THE INVENTION

This invention is generally directed to microfluidic chip devices and an automated apparatus for providing small volume, multifunction lab procedures on microfluidic chips.

BACKGROUND OF THE INVENTION

The use of microfluidic technology has been proposed for a number of analytical chemical and biochemical operations. This technology allows one to perform chemical and biochemical reactions, macromolecular separations, and the like, that range from the simple to the relatively complex, in easily automated, high-throughput, low-volume systems. The term "microfluidic" refers to a system or device having micron or submicron scale channels and chambers. In general, microfluidic systems include a microfluidic device, or chip, that has networks of integrated submicron channels in which materials are transported, mixed, separated and detected. Microfluidic systems typically also contain components that provide fluid driving forces to the chip and that detect signals emanating from the chip.

Microfluidic chips may be fabricated from a number of different materials, including glass or polymeric materials. An example of a commercially available microfluidic chip is shown in FIG. 1. FIG. 1A is a topside view of the chip, and FIG. 1B is a bottom side view of the same chip. That chip, a DNA LacChip® manufactured by Caliper Life Sciences, Inc. of Mountain View Calif., is used with the Agilent 2100 Bioanalyzer system manufactured by Agilent Technologies, Inc. of Palo Alto Calif. The chip in FIG. 1 has two major components: a working part 128 made of glass, and a plastic caddy or mount 127 bonded to the working part. The working part contains microfluidic channels in its interior, and wells on its exterior that provide access to the microfluidic channels. The working part is typically fabricated by bonding together two or more planar substrate layers. The microfluidic channels in the working part are formed when one planar substrate encloses grooves formed on another planar substrate. The mount protects the working part of the chip, and provides for easier handling of the chip by a user. The increased ease of handling partially results from the fact that the mount 127 is larger than the working part of the device, which in many cases is too small and thin to be easily handled. The mount may be fabricated from any suitable polymeric material, such as an acrylic or thermoplastic. The glass working part is typically bonded to the polymeric mount using a UV-cured adhesive. Reservoirs 129 in the mount 127 provide access to the wells on the working part of the chip. The reservoirs 129 hold much greater volumes of material than the wells in the working part 128, thus providing an interface between the macro-environment of the user and the microenvironment of the wells and channels of the microfluidic device. Although the use of the plastic mount 127 to hold the working part 128 provides several advantages, the use of the mount may have some disadvantages. For example, the polymeric material of the mount 127 may cause dye interaction and surface chemistry issues with respect to the materials applied to the reservoirs. Further, mount 127 and the adhesive used to adhere mount 127 to the working part may affect the life span of the chip when shipped and stored.

The type of microfluidic chip in FIG. 1 is a "planar" chip. In a planar chip, the only access to the microchannels in the chip is through the reservoirs 129 in the caddy and in-turn through the wells in the working part 128. Another type of microfluidic chip is a "sipper" chip, which has a small tube or capillary (the "sipper") extending from the chip through which fluids stored outside the chip can be directed into the microfluidic channels in the chip. Typical sipper chips have between one and twelve sippers. In use, the sipper is placed in a receptacle having sample material and minute quantities of the sample material are introduced, or "sipped" through the capillary tube to the microfluidic channels of the chip. This sipping process can be repeated to introduce any number of different sample materials into the chip. Sippers make it easier to carry out high-throughput analysis of numerous samples on a single microfluidic chip.

Microfluidic chips fabricated from glass are typically shipped after having been preconditioned or "primed" with sodium hydroxide under pressure. The preconditioning process prepares the surface of the chip for use and increases the lifetime of the chip. The extremely caustic nature of the preconditioning fluid makes it desirable to have the preconditioning performed by technicians prior to shipping as opposed to having the end user apply the sodium hydroxide. The chips are then shipped in liquid to preserve the preconditioned surface state. In many cases, it may also be desirable to precondition or prime microfluidic chips fabricated from polymeric materials, and to ship those chips in a liquid to preserve a preconditioned surface state. Regardless of the chip material, and the surface treatment requirements associated with that material, microfluidic chips often need to be primed, i.e. filled with liquid, before they can be used to perform analyses.

Current shipping and storage methods for primed microfluidic chips typically entail the use of a fluid-filled container. The fluid is generally distilled water containing a preservative such as EDTA or a buffer such as tris-tricine. When a chip is placed in a container, it is submerged in the fluid and suspended in the submerged position. This type of shipping container is undesirable for various reasons. First, the end user must "fish" the chip out of the fluid in which it has been shipped. Secondly, the submersion may weaken the adhesive bonding between the laminated substrate layers in the chip, or the bonding between the working part of the chip and a mounting fixture holding the working part of the chip. Those types of delamination may render the chip unusable. Finally, as the chips are capable of being reused many times, the user must replace the chips into the storage fluid between uses, which increases the risk of contaminating the chip.

Although microfluidic devices have become advanced enough that multiple analyses can be performed on a single chip using very small volumes of sample material, the preparation and handling of chips often requires a great deal of human effort and time. The reservoirs on a chip are also vulnerable to evaporation and/or current leakage between reservoirs causing changes in concentration of sample materials or in fluid flow through the chip, which can make the chip function inaccurately.

Several macro-scale automatic reader and liquid handling devices have been developed for transferring material into and out of, and monitoring the output (e.g. level of fluorescence) of reactions carried out in standard 96, 192, 384 and 1536 well microtiter plates. Such devices are particularly useful for liquid handling or detection. However, the microtiter plates used in conjunction with such macro-scale devices provide limited functionality as compared with microfluidic devices, since microtiter plates do not allow for the type fluid movement that can take place within microfluidic devices. Although the macro-scale devices designed for used with microtiter plates do have some liquid handling capability, this capability is not particularly suited for the types of operations that can be performed on microfluidic chips. Furthermore, liquid handling devices and automatic readers are not conventionally integrated into a single machine.

BRIEF SUMMARY OF THE INVENTION

The present invention is directed towards an automated microfluidic chip processing apparatus.

One aspect of the present invention is an automated microfluidic chip processing apparatus including a chip handling system, a fluid control device, and a detection system, wherein the chip handling system moves the chip to the fluid control device and detection system. In one aspect of the present invention, a liquid handling system may be integrated into the automated microfluidic chip processing apparatus.

Another aspect of the present invention includes a chip that is suitable for use in the present invention that does not utilize a mount conventionally found on microfluidic chips. Such a chip may have no mount or may use an alternative mount providing for smaller overall chip size. Yet another aspect of the present invention is a microfluidic chip with or without a mount having a pierceable film covering at least one of the reservoirs. Another aspect of present invention is a cartridge for stacking, distributing and dispensing microfluidic chips, such as for use with an apparatus of the present invention.

Another aspect of the present invention includes a method of processing a microfluidic chip including providing a microfluidic chip apparatus, including a chip handling system, a fluid control system, and a detection system. The method includes providing at least one microfluidic chip including a sample material; positioning the chip with respect to a fluid control system and a detection system via a chip handling device; controlling the flow of a material through said chip via the fluid control system; and detecting results of an assay conducted on the chip via the detection system.

Other aspects of the present invention include the apparatus described above having one or more of the following: a priming station, a washing station, a control system for controlling the apparatus, a data output system, an alignment system and/or the capability of simultaneously processing more than one chip.

Further features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art based on the teachings contained herein.

BRIEF DESCRIPTION OF THE DRAWINGS/FIGURES

The accompanying drawings, which are incorporated herein and form a part of the specification, illustrate the present invention and, together with the description, further serve to explain the principles of the invention and to enable a person skilled in the pertinent art to make and use the invention.

FIG. 3A is a schematic perspective view of an embodiment of an apparatus of the present invention.

FIG. 4C is a schematic top perspective, partial cross-sectional view of the apparatus of FIG. 4A.

FIG. 5B is a schematic top view of an alternative embodiment of a chip handling system of the present invention.

FIGS. 11A and 11B are schematic exploded views of an embodiment of an alignment system of the present invention.

The present invention will be described with reference to the accompanying drawings. The drawing in which an element first appears is typically indicated by the leftmost digit (s) in the corresponding reference number.

DETAILED DESCRIPTION OF THE INVENTION

Figure 2:
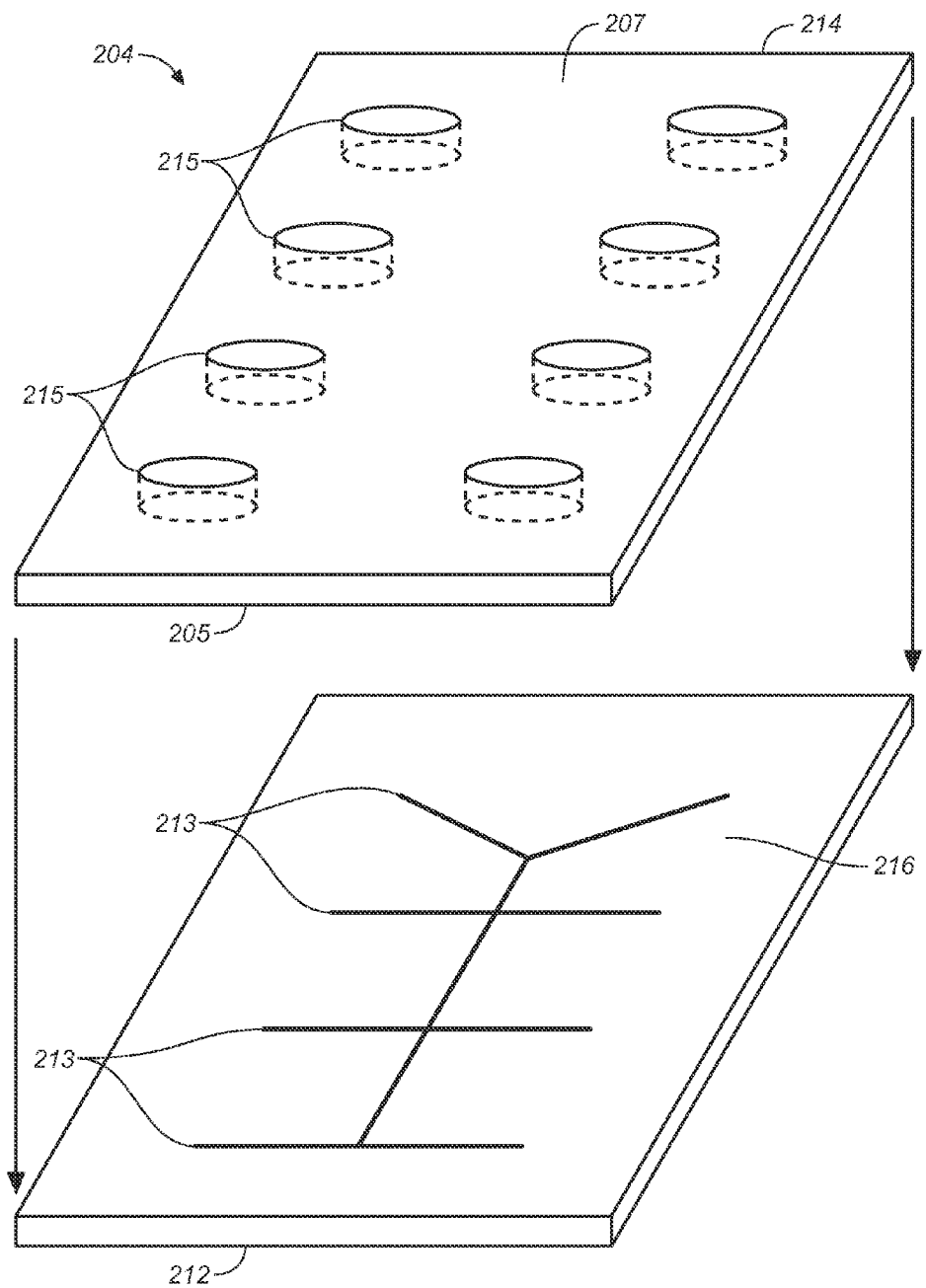
FIG. 2 is a schematic exploded perspective view of a microfluidic chip of the present invention.

The present invention is directed towards an automated apparatus for processing a microfluidic chip. An example of a microfluidic chip 204 is illustrated in FIG. 2. The chip 204 shown is the working part of the chip without a mount. In the embodiment shown in FIG. 2, the chip 204 includes a bottom plate 212 formed from a solid substrate that is substantially planar in structure, and which has at least one substantially flat upper surface 216. The substrate could be fabricated from a variety of materials such as fused silica, glass, or plastic. In this embodiment, the channels and/or chambers of the microfluidic chip 204 are formed when grooves 213 in the upper surface 216 of the bottom plate 212, are enclosed when the bottom plate 212 is bonded to a top plate 214. The grooves can be formed in the upper surface 216 of the bottom plate by any fabrication method capable of producing microscale features in the material forming the bottom plate. For example, if the bottom plate 212 is formed from a glass substrate, the grooves could be formed by photolithographically defining the location of the grooves, and then etching the grooves into the upper surface 216 of the bottom plate. If the bottom plate 212 is formed from the plastic substrate, the grooves 213 could be formed by injection molding or by embossing. In alternative embodiments, the grooves that will form the channels or chambers could be fabricated in the lower surface 205 of the top plate 214, or in both the upper surface 216 of the bottom plate 212 and the lower surface 205 of the top plate 214. Like the bottom plate 212, the top plate 214 is substantially planar in structure, and can be formed from a solid substrate of fused silica, glass or plastic. The top plate 214 has both the first surface 205 and a second surface 207 opposite the first surface 205. In the microfluidic chip shown in FIG. 2, the top plate 214 includes a plurality of apertures, holes or ports 215 disposed therethrough, e.g., from the first surface 205 to the second surface 207.

When the first surface 205 of the upper plate 214 is placed into contact with and bonded to the upper surface 216 of the bottom plate 212, the grooves and/or indentations 213 in the surface of the bottom plate 212 are enclosed to form microchannels and/or chambers. The apertures, holes or ports 215 disposed in the upper plate 214 of the chip are oriented such that they are in communication with at least one microchannel and/or chamber formed from the grooves or indentations 213 in the bottom plate 212, thus providing external access to the microscale channels and chambers. In other words, the apertures form wells that facilitate fluid or material introduction into the microchannels, as well as to provide ports through which electrodes or pressure hoses may apply electric fields or pressure differentials for controlling and directing fluid transport within the microfluidic chip. The wells typically hold about 500-5000 nl and have diameters of about 500 µm to 2000 µm.

The operation of a microfluidic chip includes the movement of material through microchannels arranged on the chip in a controlled manner. Several different methods have been used to control the flow of material in a microchannel, and each may be incorporated into embodiments of the present invention, as a fluid control system. For example, fluid movement may be controlled by the application of positive or negative partial pressure to certain reservoirs, so that fluid moves from locations of high pressure to locations of low pressure through the microchannels. Partial pressures may be applied by a pumping mechanism or the application of a vacuum force to a reservoir. Another example includes the use of electro-kinetics, such as electrophoresis or electro-osmosis, wherein the fluid moves in response to the application of positive and negative voltages. Therefore, the fluid control system includes the capabilities for providing and controlling forces to move fluids through microfluidic channels.

An embodiment of the apparatus of the present invention also includes a detection system in operation with the chip to provide data regarding the concentration of one or more materials in a microfluidic channel. The features that a detection system may detect to provide concentration information include, but are not limited to, optical absorbance, refractive index changes, fluorescence emission, chemiluminescence, Raman spectroscopy, electrical conductance, electrochemical amperiometric measurements, and acoustic wave propagation. These various detection methods are discussed, for example, in U.S. Pat. No. 5,858,195, the disclosure of which is incorporated herein by reference in its entirety. In one embodiment, the detector system is capable of detecting more than one sample material in a microfluidic chip, if desired.

Embodiments of the present invention provide systems and methods for automating these and other aspects of chip handling and operation for increased accuracy and speed in the biological and chemical analyses performed on microfluidic chips. For example, FIG. 3A shows an apparatus 300 in which multiple microfluidic chips, such as chip 204, can be used. The apparatus includes a deck 302 and a robotic head 306 that is capable of moving in the x-y-z directions across deck 302. Robotic head 306 is suspended from a hood 308 that is supported by supports 310. Deck 302 has been divided into universal stations 320. Universal stations 320 may contain any type of materials, plates, holders, etc., that may be used during the microfluidic chip processing.

In the embodiment of FIG. 3A, robotic head 306 also incorporates a liquid handling device. In order for a microfluidic chip to operate, sample and buffer material must be added to the reservoirs on the chip. The liquid handling system provides materials to chip 204 for various procedures. The liquid handling device can be any automated apparatus for transferring liquid. The liquid handling system may transfer liquid from bulk storage or may transfer liquid materials from macro-volume receptacles to a micro- or nano-volume receptacle. For example, a liquid handling system may be capable of transferring sample material, buffer, or other materials into the micro-, nano-or Pico-volume reservoirs of the microfluidic chip 204.

The liquid handling system may be a capillary or other pipetting system using a volume control, to aspirate and dispense materials. Examples of such volume controls include, but are not limited to, peristaltic pumps, syringe pumps, solenoid inertial dispensing systems, flowmeters, or piezoelectric transducer controls. The liquid handling system may include any type of nozzle for directing the material into the reservoirs of the microfluidic chips. One example of a liquid handling system with nano-volume capacity includes an array of stainless steel cannula, each having a ceramic nozzle that can deliver volumes as low as 100 nl. U.S. Pat. No. 6,592,825, the disclosure of which is incorporated by reference herein in its entirety, discloses the transfer of even smaller volumes of material to and from microfluidic plates, for example, picoliter volumes, which may be incorporated into the present invention. An array of disposable tips may be used or a fixed cannula with permanent tips. In one aspect of the invention, the liquid handling system may have an interchangeable arrangement of tips and arrays for a variety of liquid handling procedures.

Disposable tips and other features of the liquid handling device may be provided in one or more of the universal stations 320 provided in deck 302. The liquid handling system is generally capable transferring materials from any sized receptacle, including but not limited to, a flask, a bulk resource, an eppendorf tube, and wells on a 96-, 192-, 384- or 1536-well microtiter plate. As such, in the apparatus shown in FIG. 3A, most universal stations 320 are configured to be about the size of a standard microtiter plate. Having stations of this size allows for the placement of microtiter plates on deck 302, as a source of sample material or other materials to be added to the microfluidic chip during processing. As such, the liquid handling device of the apparatus takes sample material from a microtiter plate and applies it to a microfluidic chip positioned in a different station 320. Further, known liquid handling devices currently available for use with microtiter plates may be appropriate for incorporation into the apparatus of the present invention. In other embodiments, some or all of the stations 320 on deck 302 are the size of a single microfluidic chip, a microfludic chip mount of a particular size, or an undiced microfluidic chip wafer featuring a plurality of microfluidic chips, as discussed below with respect to FIG. 9. Alternatively, stations 320 may be occupied by a holder/adaptor for holding one or more microfluidic chips.

Further, the liquid handling system may include such advanced features as the ability to dilute or normalize concentrations of materials in a single step procedure. The liquid handling system may also be capable of supplying consistent small volumes to reservoirs for the formation of consistent streams flowing through microchannels. Further, the liquid handling system may by self-cleaning. In other words, it may have the ability to flush the liquid handling device to avoid contamination between different samples. Thus, the liquid handling device is capable of handling a variety of materials at a time, with appropriate washing between each material. Further, a liquid handling device of the present invention may be capable of providing a sample plug of material in a buffer stream, to process several samples in spaced out intervals on a chip 204. Possible sample/pipette configurations include, but are not limited to: one pipette for a single sample, one pipette for multiple samples, multiple pipettes for a single sample, and multiple pipettes for multiple samples. Also, data analysis performed by the liquid handling system can confirm in real-time whether the current volume of material has been properly transferred to a reservoir and can perform repeat pipetting, if necessary.

The apparatus 300 includes at least a fluid control system and a detection system, disposed in a single unit 317. In the embodiment of FIG. 3A, unit 317 is disposed on deck 302, occupying one or more universal stations 320. Head 306 also functions as a chip handing system to move a chip 204 from a station 320 on deck 302 to the unit 317, where the fluid control system and detection system operate on chip 204. As shown in FIG. 3A, head 306 includes a gripper 321 capable of moving a single microfluidic chip, several microfluidic chips or other items occupying stations 320. Microfluidic chip 204 is acted upon by a liquid handling system operated from within head 306. Once the material is loaded on to the chip 204 via the liquid handling system located in head 306, head 306 moves chip 204 to unit 317.

Figure 3B:
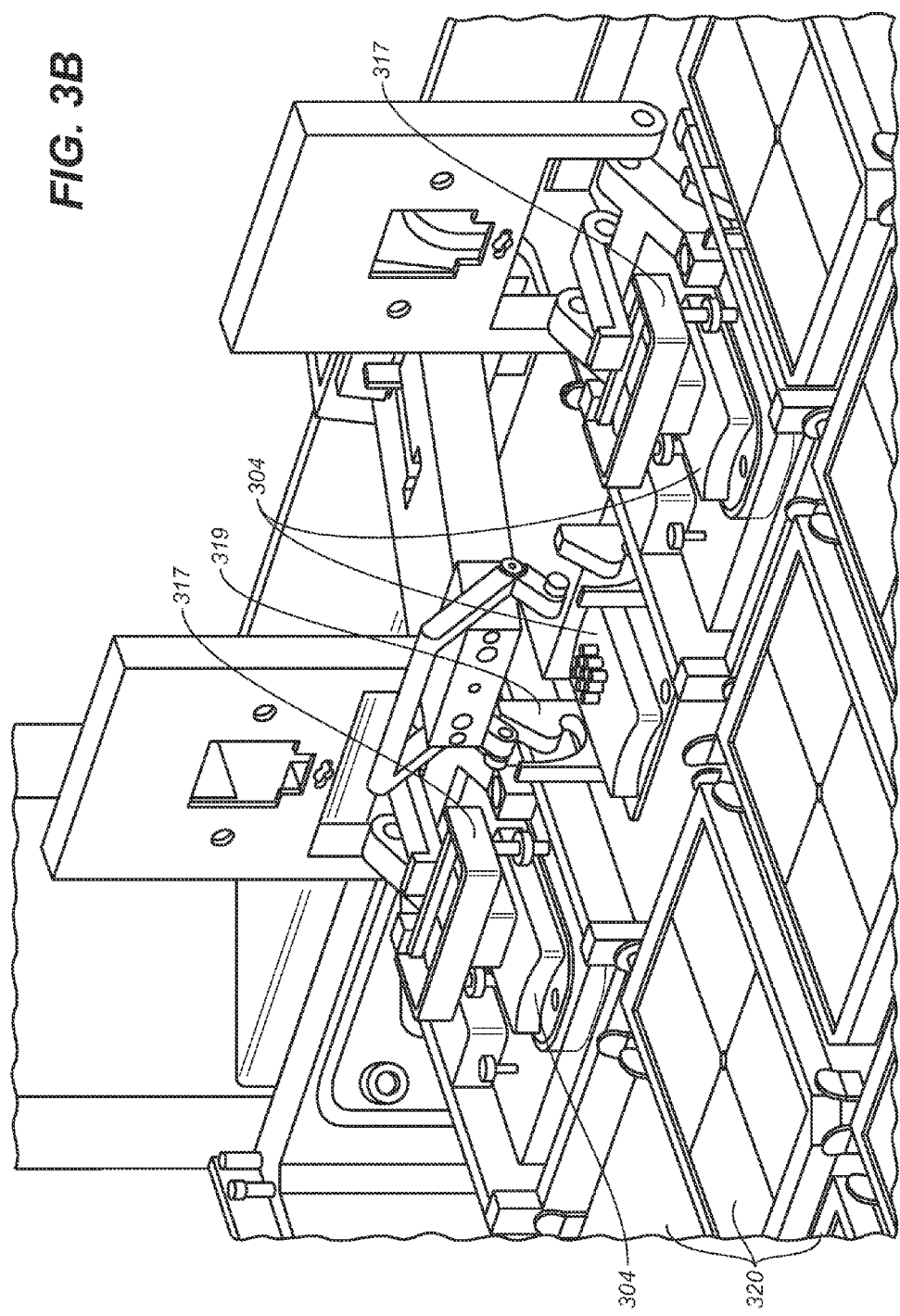
FIG. 3B is an exploded view of a portion of the apparatus of FIG. 3A.

Chip 204 may, however, first be moved to a priming station 319 also positioned on deck 302. FIG. 3B is a view of two units 317 that include the fluid control system and the detection system. FIG. 3B also shows a priming station 319 that is used to begin the flow of material through the microchannels of chip 204. Microfluidic chips are often primed with gel, buffer or another such material. Chip 204 is then placed in one of the two units 317, wherein the desired operation is performed on the chip 204 by the controlled flow of the material through the chip and the results determined by the detection system.

The apparatus 300 of FIG. 3A may also include a washing or flushing system (not shown), where chip 204 and/or the liquid handling system can be flushed and/or a shaking system, whereby the chip is shaken and any materials thereon are mixed or stirred.

FIG. 3B shows a chip 304 positioned in units 317. Chips 304 include a chip substrate and a mount. However, a chip 204 without a mount may be used instead, as discussed below in greater detail. In the examples shown in FIGS. 3A and 3B, electrodes positioned in a hinged lid of units 317 are lowered to engage reservoirs of a pre-positioned microfluidic chip. In other embodiments, the fluid control system and detection system may be positioned on deck 302 in other ways. For example, in one embodiment, these features are disposed in head 306, which moves with respect to deck 302, such that each feature can access the chip 204 from above. In yet another embodiment a liquid handling device is also positioned on deck 302 and head 306 functions merely as a chip handling system to move chip 204 from the station or stations occupied by the liquid handling system to the station or stations occupied by fluid control system and detection systems.

Figure 4A:
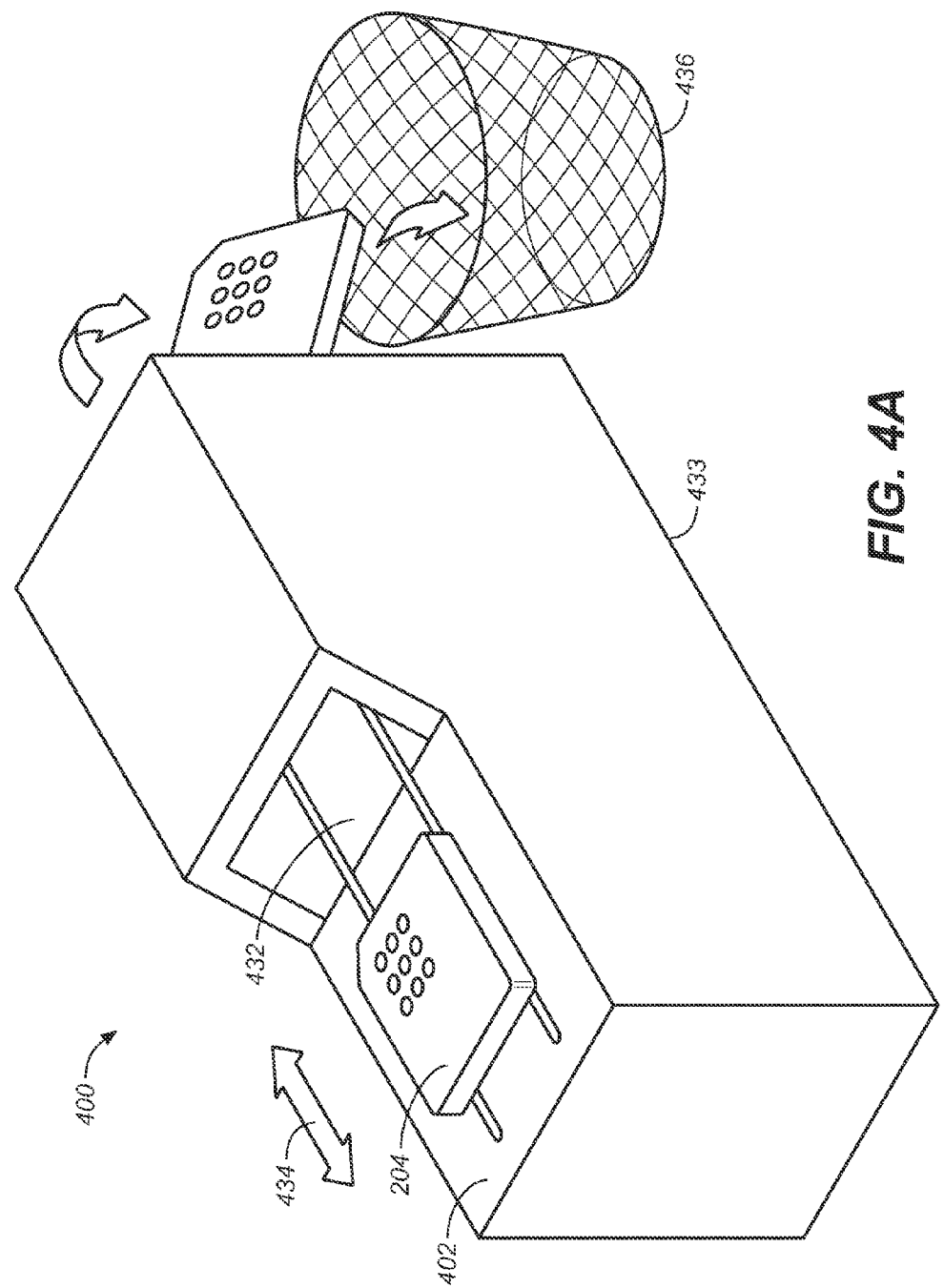
FIG. 4A is a schematic top perspective view of an alternative embodiment of an apparatus of the present invention.
Figure 4B:
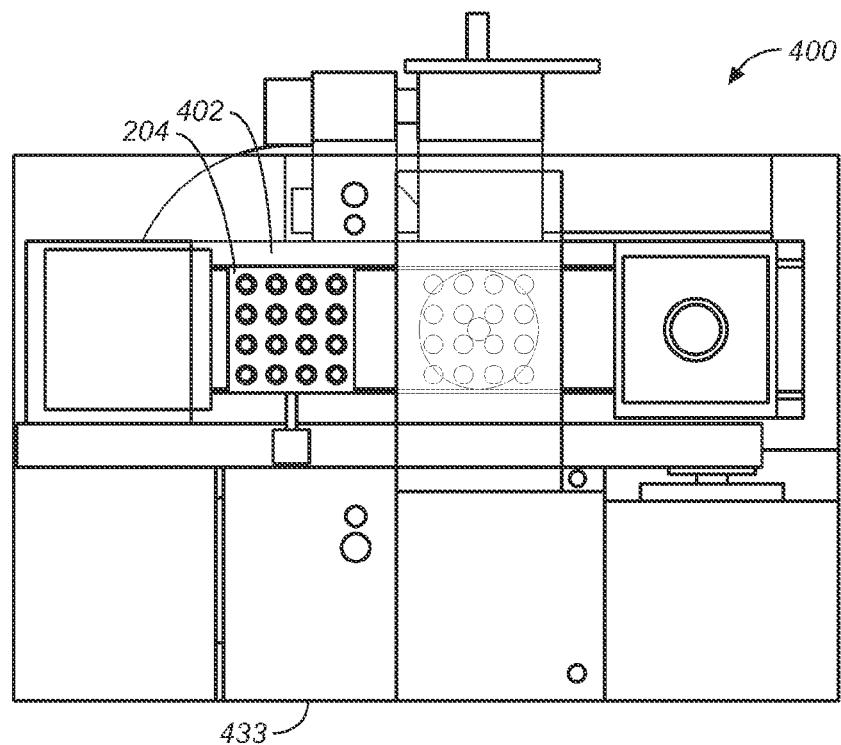
FIG. 4B is a schematic top view of the apparatus of FIG. 4A in combination with a top plan view of a conventional 96-well microplate.
Figure 4B:
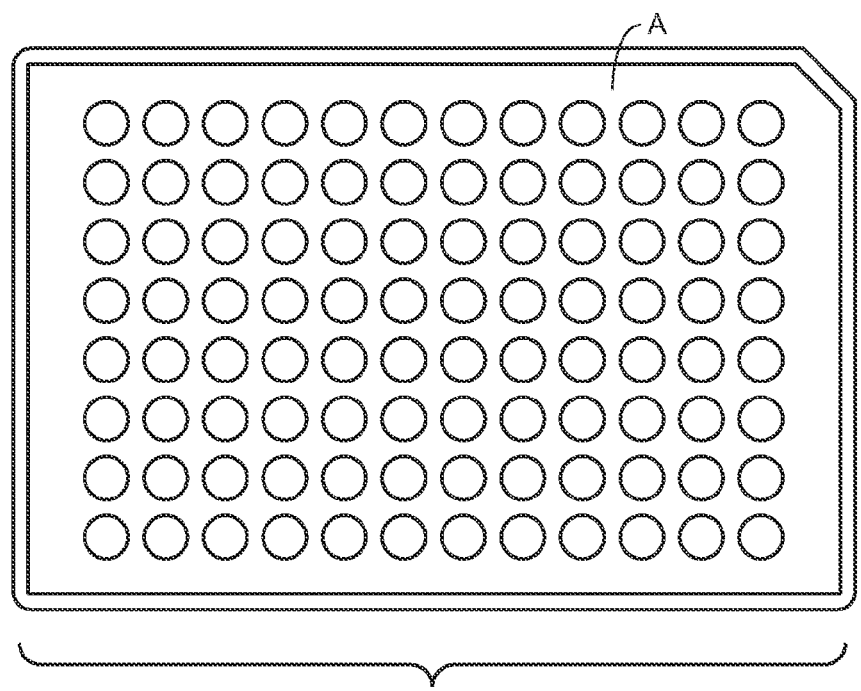

Another embodiment of an apparatus of the present invention is shown in FIGS. 4A-4C. FIG. 4A shows an apparatus 400, which includes at least the fluid control system and the detection system, located within a housing 433. The apparatus 400 includes a deck 402 onto which a microfluidic chip 204 has been placed. The chip 204 is positioned on a moving conveyor 432, which delivers the chip 204 in the direction indicated by arrow 434 into and out of housing 433. After the microfluidic chip is processed, conveyor 432 may move the chip out of housing 433 in a direction opposite where it entered, so that the chip may be disposed into a receptacle 436. As such, the embodiment shown in FIG. 4A is particularly useful for disposable microfluidic chips 204 that are not intended to be reused. It is intended, however, that apparatus 400 may be used with either reusable or disposable microfluidic chips 204.

Apparatus 400 of the present invention does not necessarily incorporate a liquid handling system. In this embodiment, a liquid handling system may act upon a microfluidic chip 204 while it is positioned on deck 402, outside of housing 433, as shown in FIG. 4A. Alternatively, liquids may be supplied by hand to chip 204, or by some combination thereof. In another embodiment, a liquid handling system may be integrated into apparatus 400, such as by having deck 402 be a station in a liquid handling system. The in and out movement of conveyor 432 allows a chip, for example, to be loaded with material on deck 402, moved into housing 433 to be primed by the fluid control system, moved back to deck 402 to reload with sample material, and moved again into housing 433 for processing.

FIG. 4B shows a top view of the apparatus 400, showing the placement of chip 204 on deck 402 and within housing 433. FIG. 4B also shows the size of the apparatus relative to a conventional 96-well microliter plate A. It is intended that the apparatus 400 have the same size footprint as conventional microtiter plate A. Since the size of the apparatus 400 is roughly the dimensions of microliter plate A, it may be positioned to occupy one or more of the universal stations 320 in an apparatus 300 such as that shown in FIG. 3A, which integrates a liquid handling system therein. In other words, apparatus 400 would replace the unit 317, shown in FIG. 3A.

FIG. 4C shows a schematic perspective view of the working parts of the apparatus 400, which are enclosed in a housing, such as housing 433 of FIG. 4A. FIG. 4C shows chip 204 positioned on deck 402. In this position, chip 204 is accessible to a liquid handling system, if desired. In an alternative embodiment, apparatus 400 may have a deck that slides into and out of housing 433, similarly to a CD player sliding in an out of a dashboard car CD player.

Apparatus 400 includes an upper hood 440. In the example shown in FIG. 4C, the upper hood 440 includes a fluid control system, shown in phantom in FIG. 4C as electrode array 444. Meanwhile, below deck 402 lies a hydraulic or pneumatic lift arrangement 446. The lift arrangement 446 includes a hydraulic or pneumatic actuator, such as a motor 445 and a platform 447. When actuated, platform 447 is hydraulically or pneumatically extended in a vertical direction, lifting the chip 204 off deck 402. Platform 447 may also be hydraulically or pneumatically retracted to reposition chip 204 on deck 402. When the platform 447 is in the extended position, chip 204 engages the electrodes 444 of the fluid control system located in the upper hood 440. Thus, the fluid control system only operates upon chip 204 when the chip is pressed against it.

In an alternative embodiment, upper hood 440 may instead move in a vertical direction to bring the fluid control system into contact with chip 204. In still another embodiment, a hydraulic or pneumatic lifting device may be positioned in the upper hood 440, such that the device pulls the chip 204 toward the electrode array 444 rather than pushing from beneath chip 204. Because upper hood 440 is positioned above chip 204, a variety of fluid control devices are easily substituted for each other.

Similarly, a detection system may either be disposed in the upper hood 440 along with the fluid control system, or it may be integrated within the lift arrangement 446, such as incorporated as part of platform 447. In the embodiment of FIG. 4C, the center of platform 447 includes an optical detector 443 as part of a detection system. Platform 447 may also include a heating and/or cooling system, since the viscosity of fluids moving through microchannels is greatly affected by temperature changes. The heating and/or cooling system may also include thermocouples for measuring the temperature of fluids in microchannels and a temperature control system. Further, platform 447 may incorporate an optical alignment system, such at that discussed in detail below with respect to FIG. 11.

Apparatus 400 includes a chip handling system that features conveyor 432 to move chip 204 across deck 402. Conveyor 432 includes a motor 450 that rotates at least one of a pair of spindles 448 to move a belt 449. Spindles 448 may also be pulleys, gears, or other devices for moving a belt 449. Conveyor 432 also includes at least one car 451 attached to the belt 449. In this case, car 451 includes a rod 452 that engages a notch 409 in chip 204, to move chip 204 along deck 402.

Figure 5A:
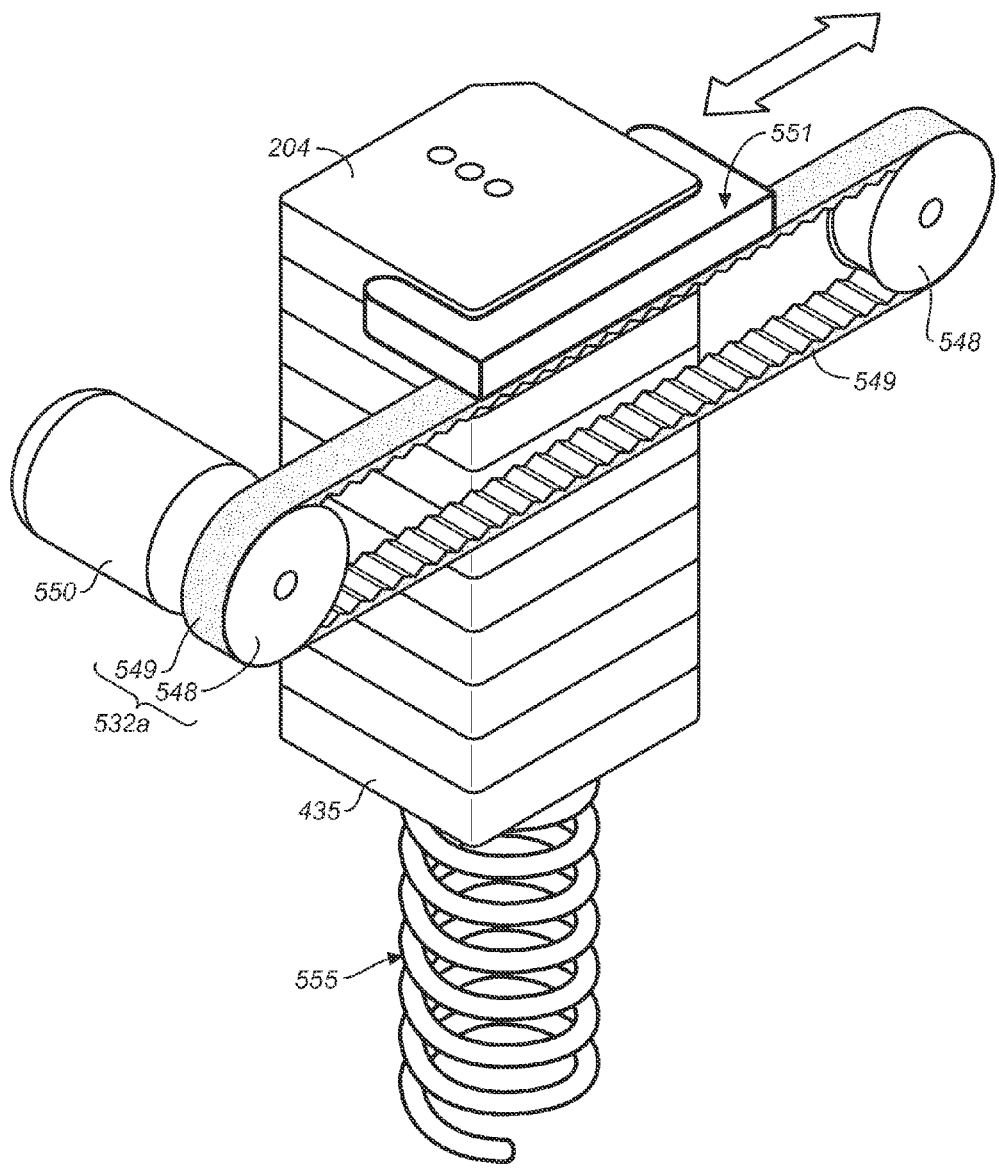
FIG. 5A is a schematic perspective view of an embodiment of a chip handling system of the present invention.

FIG. 5A shows another embodiment of a chip handling system that could be used in apparatus 400, which includes a conveyer 532*a* having a belt 549 and spindles 548, one or both of which are rotated by a motor 550. Attached to belt 549 is car 551, into which chip 204 is positioned, such that it is pushed along belt 549 from the sides of chip 204 rather than from a notch in the middle of the chip, as shown in FIG. 4C. In one embodiment, conveyor 432 may use rollers instead of spindles 448 and belt 449 to move a chip 204. In another embodiment of a chip handling system, in FIG. 5B, a conveyor 532*b* may consist of two belts 549*a* and 549*b* for transporting the chip 204 into and out of the housing 433 and positioning chip 204 on platform 447. In this case, belt 549*a* is positioned under one side of chip 204 and belt 549*b* is positioned under the opposite side of chip 204, such that platform 447 has access to a central area of chip 204 between belts 549*a* and 549*b* to lift it. In this embodiment, conveyor 532*b* of FIG. 5B does not require a car to aid in moving chip 204 along deck 402. In one embodiment, conveyor 532*b* may use rollers instead of spindles 548 and belts 549*a*/549*b* to move a chip 204.

Each of apparatus 300 and apparatus 400, described herein may be utilized with more than one chip 204 for continuous chip processing. FIG. 4C shows a stack 435 of chips 204. In this manner, microfluidic chips 204 can be processed rapidly and repeatedly without having to manually load and unload each chip 204. FIG. 4C also shows a bucket 465, into which is inserted a cartridge 460 holding stack 435 of chips 204. Thus, in another aspect of the present invention, microfluidic chips 204 are not packaged separately, but are instead packaged in stacks 435 that are stored in cartridges 460.

Figure 6A:
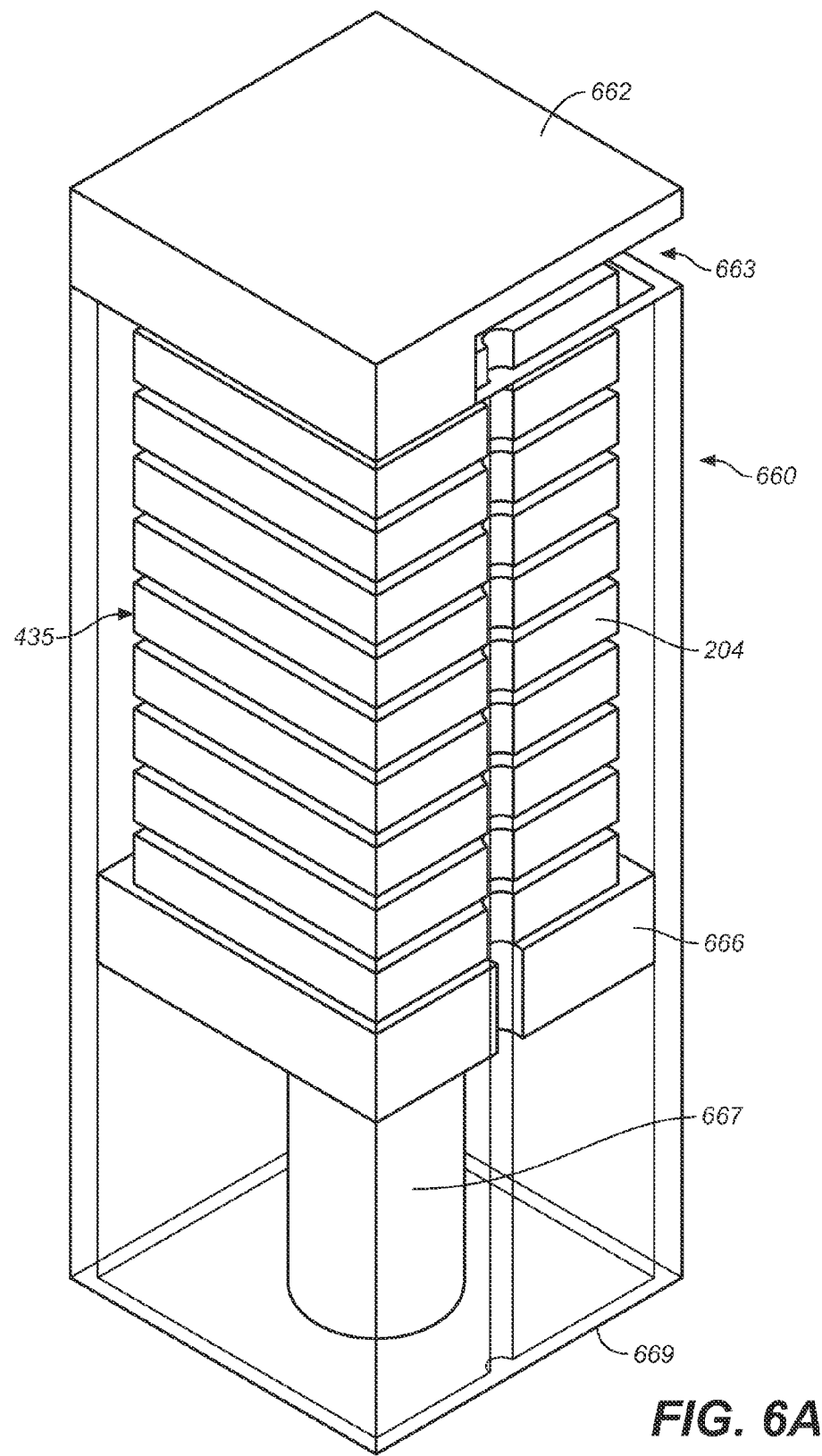
FIG. 6A is a schematic top perspective view of an embodiment of a chip cartridge of the present invention.

FIG. 6A shows an example of a cartridge 660 with chips 204 housed therein. Cartridge 660 also includes a lid 662, which may be either automatically lifted by an apparatus of the present invention when a new chip is desired or which may have a slot 663 through which each chip 204 is accessed. Alternatively, stack 435 could be shrink-wrapped and shipped without an exterior cartridge. Chips may be shipped in a pre-primed condition. For example, stack 435 of chips may be loaded with an electrophoresis gel or loaded with a dry material, such as a particular reagent, which can subsequently be reconstituted prior to use. However, chips may also be stacked and packaged dry, where the apparatus of the present invention includes automated priming of the chips.

Figure 6B:
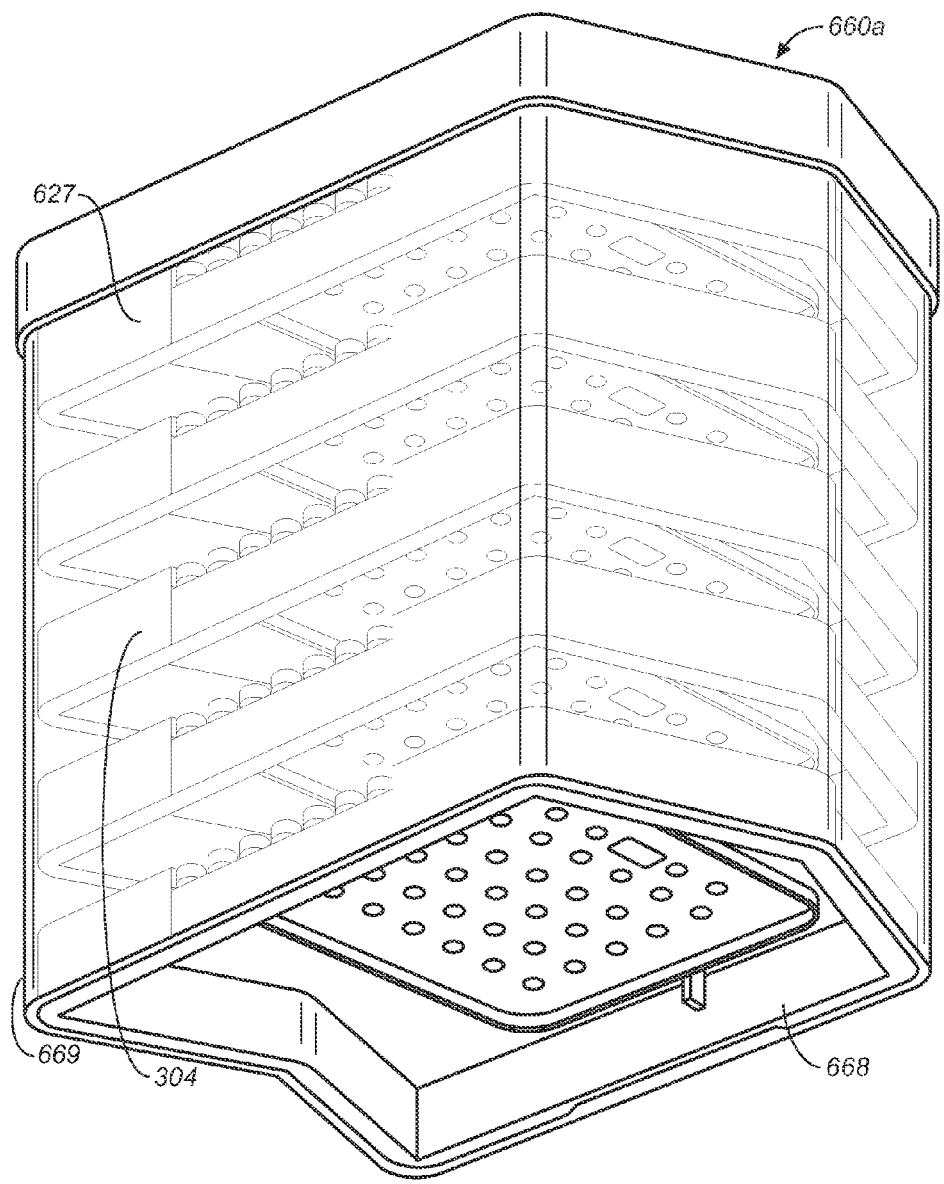
FIG. 6B is a schematic bottom perspective view of an alternative embodiment of a chip cartridge of the present invention.

FIG. 5A further shows how stack 435 may be biased upwards by a spring 555, such that as chips 204 are removed from the stack, a new chip 204 is pushed up to the deck 402 ready perform the next analysis. Alternatively, as shown in FIG. 6A, stack 435 may be lifted by a second hydraulic or pneumatic lift device, which includes a platform 666 and a piston 667 wherein the platform is inserted into a bottom end 669 of cartridge 660 to access the chips. In another embodiment, a cartridge 660*a*, as shown in FIG. 6B, may have an opening 668 at a bottom end 669 to be accessed by the hydraulic or pneumatic lift device. The cartridge 660*a* is configured to house microfluidic chips 304 that utilize a plastic mount 627. In particular, these mounts 627 may have the same dimensions as a microtiter plate, such that cartridge 660*a* may fit in a universal station 320 in apparatus 300 in FIG. 3A. In yet another embodiment, a cartridge with an opening 668 in a bottom end 669 may also be positioned above a deck 402. As such, gravity causes the next chip 204 to fall onto deck 402 when a bottom chip 204 is removed.

Returning to FIG. 4C, a similar bucket 436 may be provided for disposing of chips 204 after they have been processed. Bucket 436 may also include an empty cartridge 461, which is filled by the processed chips as they move along the conveyor 432, such that human contact need only occur with a cartridge and not the actual chips. Further, bucket 436 may include a washing or flushing system to clean the processed chips, such that chips may be easily reused. In another embodiment, bucket 436 may be connected with bucket 465 via a U-shaped tunnel running underneath the apparatus (not shown). In this embodiment, once a chip falls into bucket 436 and is washed or flushed, the chip is conveyed by another chip handling system so as to be restacked, for example from the bottom, in bucket 465. Constantly recycling chips in this manner provides constant access to fresh chips without requiring new cartridges for bucket 465.

Figure 7:
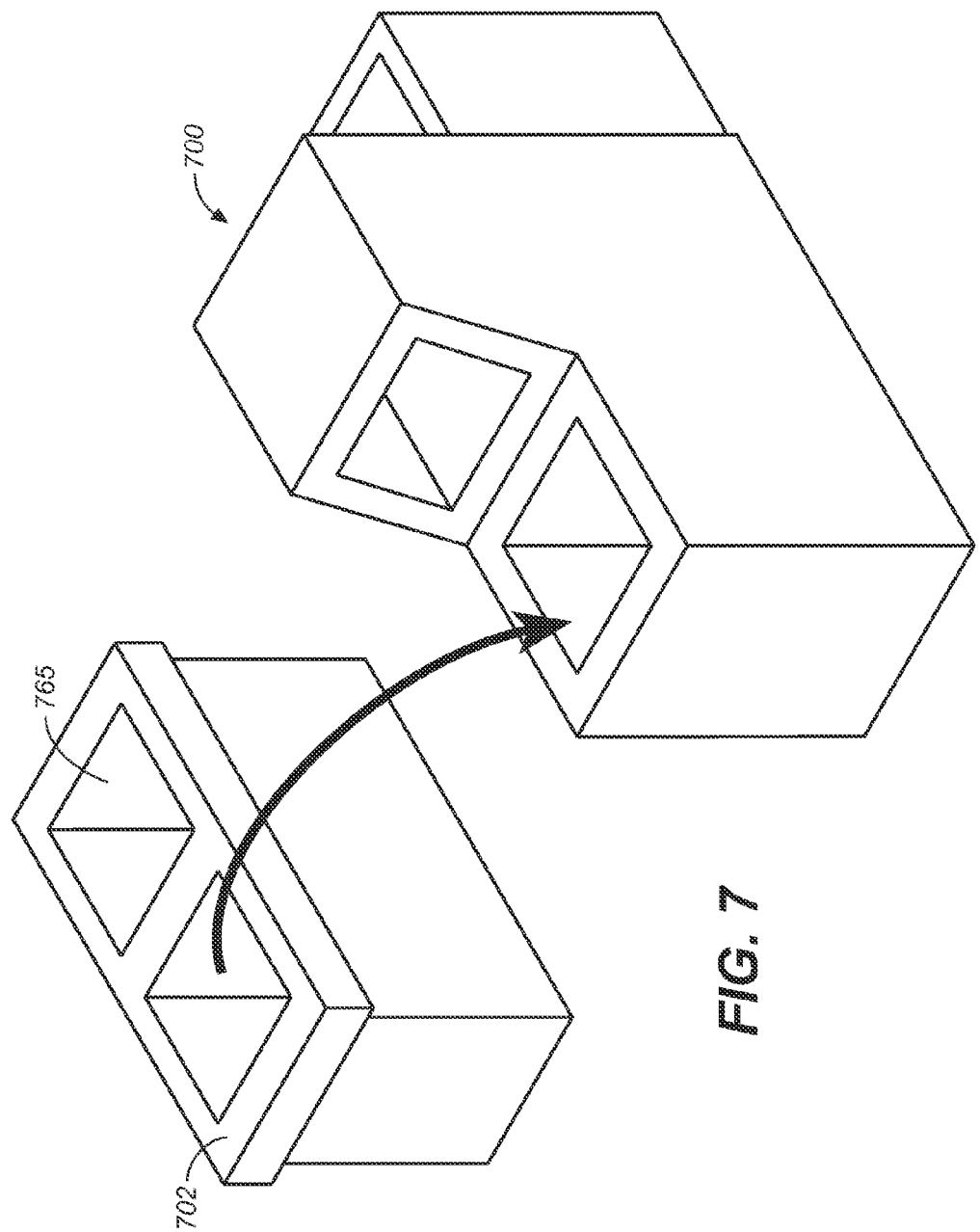
FIG. 7 is a schematic top perspective, partially exploded view of an alternative embodiment of the present invention.

FIG. 7 shows yet another alternative apparatus 700, which is identical to that of apparatus 400 except that apparatus 700 includes a removable deck 702. Deck 702 includes two or more buckets 765 for storing more than one cartridge of microfluidic chips 204. In the embodiment shown in FIG. 7, for example, there are two buckets 765 for storing two cartridges of chips 204. As such, apparatus 700 may include multiple fluid control systems, multiple detection systems and optionally multiple liquid handling systems, in order to process multiple chips 204 at the same time.

Figure 8:
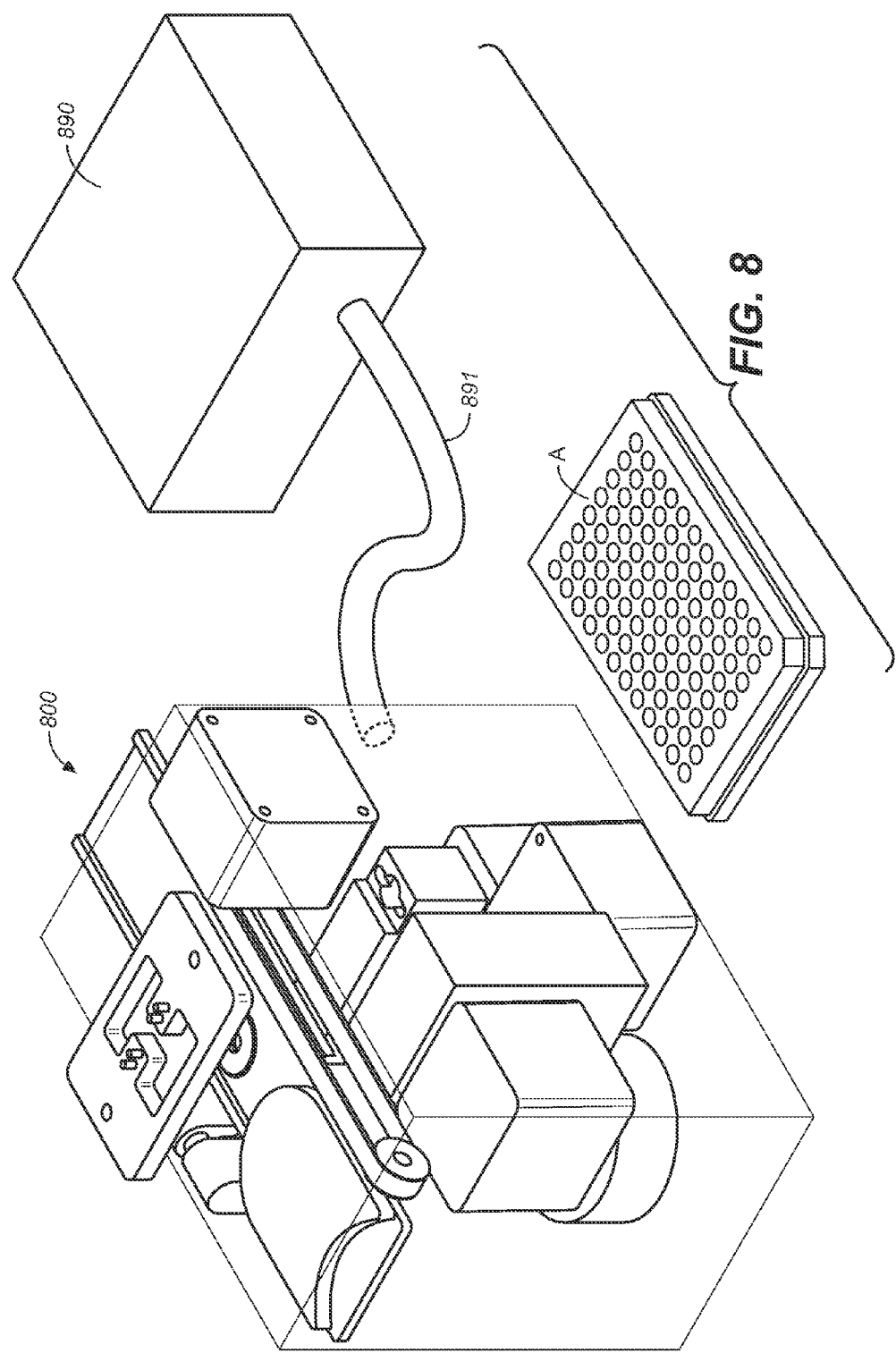
FIG. 8 is a schematic top perspective, partial cross-sectional view of an alternative embodiment of the present invention.

An apparatus of the present invention may also include software to control the operations of an apparatus of the present invention. FIG. 8 shows a control unit 890 connected via a cable 891 to an apparatus 800 of the present invention, similar to apparatus 400 discussed above with respect to FIG. 4C. Control unit 890 may include electronics, power supply, pumps or other pressure controls for the fluid control device, temperature controls for heating or cooling systems of apparatus 800 and other control and operation features, such as for the detection system and liquid handling devices. Further, control unit 890 may include any necessary software and a processor including programming for the various components described above. In one embodiment, an input device (not shown) such as a mouse, display and/or keyboard, is connected to control unit 890, such that a user can customize the particular procedures prior to and during the processing of a microfluidic chip. Further, software will function with the detection system and/or liquid handling system in order to produce real-time feedback and display of data. Such data may be made available through an output device (not shown), which is in communication with control unit 890, and which may take the form of a printer, an ethernet connection, a floppy disk or CD-ROM drive, a monitor or other visual display device. Alternatively, each of the features of control unit 890 may be integrated into the apparatus 800 itself. However, having an external control unit has the advantage that the apparatus 800 may be made smaller, such as to match the size of the footprint of 96-well microtiter plate A, as discussed above.

Control unit 890 may also be a universal control unit. As such, control unit 890 may be used with a variety of microfluidic chip processing apparatuses, which may function in different ways or be particularly designed for specific chemical or biological analyses.

Figure 1A:
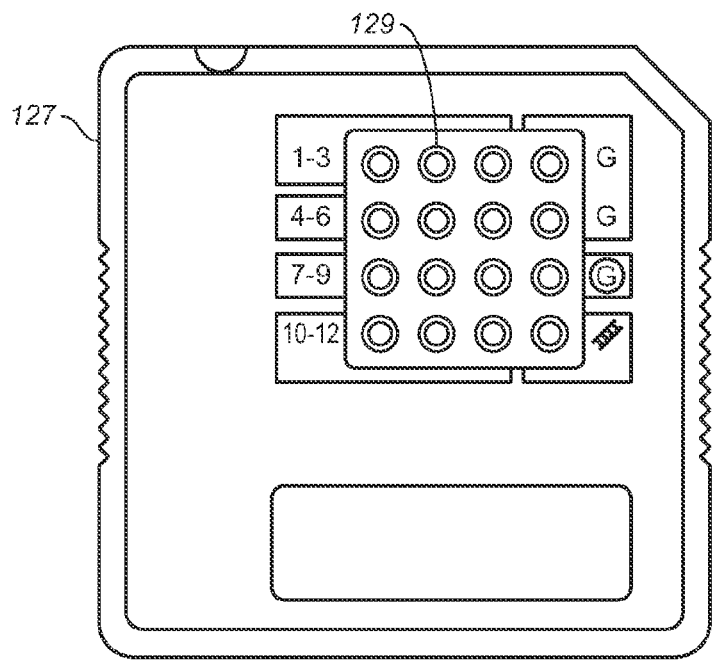
FIG. 1A is a top view of a conventional microfluidic chip.
Figure 1B:
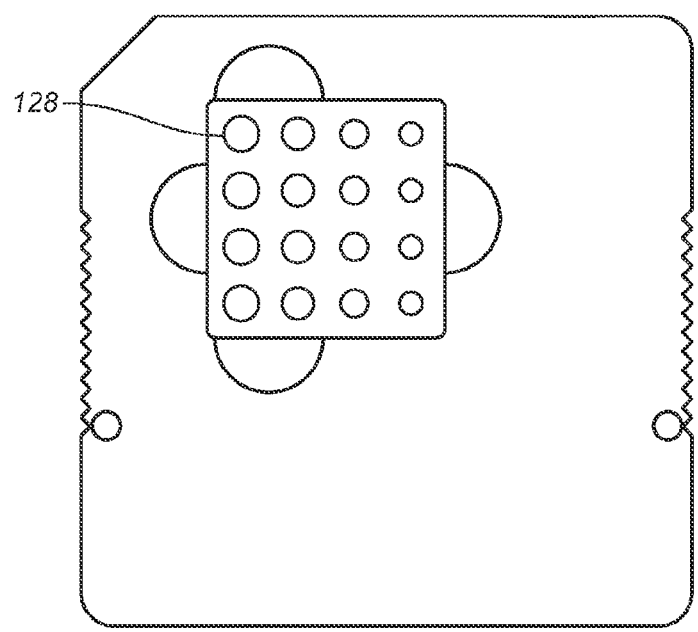
FIG. 1B is a bottom view of a conventional microfluidic chip.

A chip 204, as shown in FIG. 2, for use with an apparatus of the present invention may not require the plastic mount 127 shown in FIG. 1. Accurate liquid handling and the reduction of human interaction makes the plastic mount 127 unnecessary. Thus, manufacturing time and parts are reduced, creating more efficient manufacturing, packaging and storing of microfluidic chips 204.

There are further advantages to removing mount 127. For example, because there is no adhesive used to attach the substrate to the mount, it is easier to determine the shelf life of the chip. Further, potential dye interactions with the mount are potentially eliminated.

Since microfluidic chip 204 can be washed and/or primed at the point of use by apparatus 300/400, the chips can be stored or shipped dry for improved aging and lifetime, as well as reduced shipping and storage costs. Also, polymer mounts and adhesives are known to contaminate samples, which could make some conventional chips 104 unsuitable for use with mass spectrometers. However, without mount 127, one possible impediment to interfacing chip 204 with a mass spectrometer is eliminated.

Figure 9:
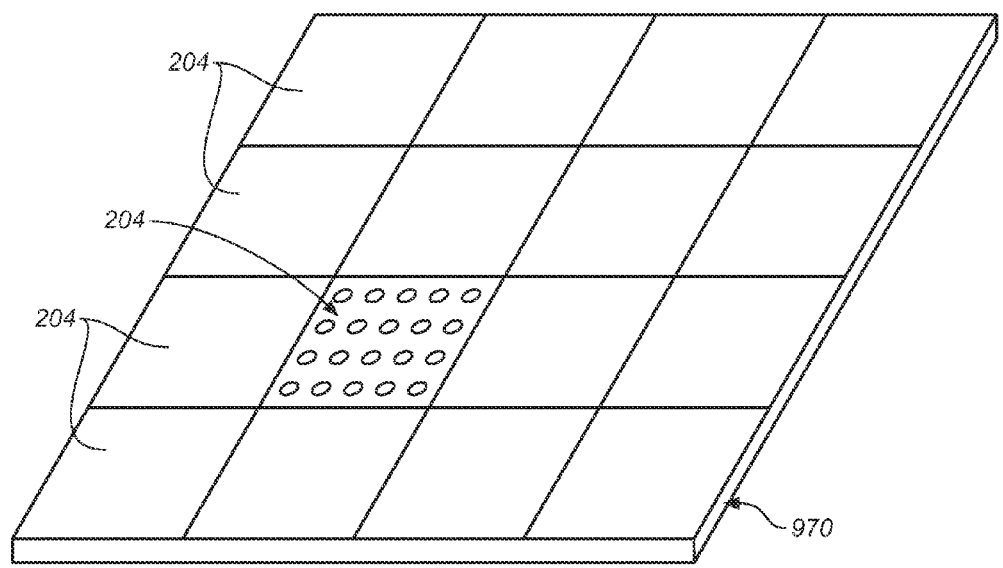
FIG. 9 is a schematic top perspective view of an undiced wafer of the present invention.

As shown in FIG. 9, microfluidic chips 204 are often made several at a time on a glass, silica or plastic wafer 970. For most applications, wafer 970 is diced to form individual chips 204. However, in an embodiment of the present invention, an apparatus, such as apparatus 300 and 400 described in detail above, may act upon more than one chip 204 at a time by acting on a undiced wafer 970. For example, an undiced wafer 970 may occupy a universal station 320 of the apparatus 300 of FIG. 3A. Similarly, an undiced wafer 970 rather than a single chip may be transported by conveyer 432 in apparatus 400 of FIG. 4C.

Figure 10A:
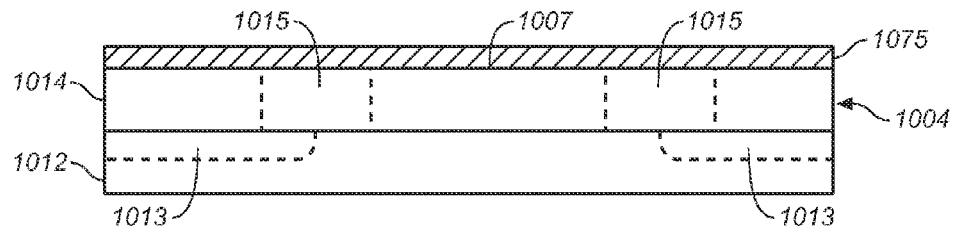
FIG. 10A is a schematic cross-sectional view of an alternative embodiment of a microfluidic chip of the present invention.

Small volumes of material are vulnerable to evaporation. Thus, FIG. 10A shows yet another microfluidic chip 1004 that is suitable for use in an apparatus of the present invention. Chip 1004 is similar to chip 204 of FIGS. 2A and 2B in that it has a first plate 1012 including a microchannel 1013 and a second plate 1014 having a reservoir 1015 bored therein. Chip 1004, however, also includes a film 1075 adhered to a surface 1007 of second plate 1014. Film 1075 covers at least reservoirs 1015, and may cover the entire chip 204, as shown in FIG. 10A. Film 1075 is a pierceable film, which can be pierced by a cannula or tip of a liquid handling device or by the application of heat, e.g. IR. As such, the film 1075 is pierced at the point when the material is added to the reservoir(s) 1015, forming only a very small hole accessing reservoir(s) 1015. Thus, evaporation from reservoir(s) 1015 is minimized. Also, film 1075 maybe a self-sealing film, such as a split septum, such that a small piercing for the purpose of filling reservoir 1015 may be resealed when the tip or cannula of a liquid handling device is removed.

Further, film 1075 may provide electrical isolation between reservoirs 1015 that are located close together. For example, if electrodes engage chip 1004 as part of the fluid control system, the electrode will also pierce film 1075 in more than one reservoir 1015 location. As such, the film 1075 will act as an insulator between adjacent electrodes. As an alternative, concentric trenches may be partially etched into the second plate 1014 to increase the path length and thus the electrical impedance from reservoir to reservoir. Still further, the film 1075 may serve as a gasket for pressurized priming and washing of chip 1004.

Figure 10B:
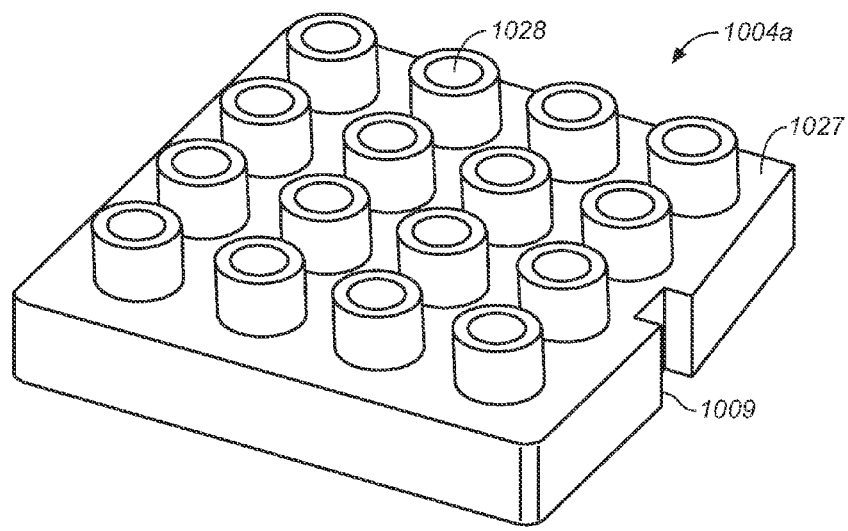
FIG. 10B is a top view of an alternative embodiment of a microfluidic chip of the present invention.

FIG. 10B shows yet another microfluidic chip 1004a of the present invention that includes a mount 1027. Since a chip 1004a that is used in an apparatus of the present invention does not require human handling, mount 1027 may be roughly the size of the microfluidic chip itself, and thus much smaller than a conventional mount 127, shown in FIG. 1. Mount 1027 includes wells 1028 to aid in the application of materials to chip 1004a by either a liquid handling system or a human operator. Further, mount 1027 provides an external location for a notch 1009 to be used for a car of a conveyor to engage the chip. Thus, such a notch 1009 need not be made in the microfluidic chip itself.

An apparatus 300/400 of the present invention may also include an alignment system to ensure that a liquid handling system, fluid control system or the detection system is properly aligned with a particular reservoir of a microfluidic chip. In an example of an alignment system in accordance with the invention, the reservoirs of a microfluidic chip are formed from non-opaque holes in a generally opaque second plate, which is bonded to a transparent first plate. Therefore, visible emission of light from a source will only be visible from an optical sensor when the light is positioned directly below a reservoir of the chip. Thus, an optical sensor can detect when it is properly aligned with a reservoir, and when a reservoir is properly positioned on a deck. Once one reservoir is detected, the locations of all additional reservoirs may be computed. Larger multi-chip wafers 970, such as discussed above in FIG. 9, reduce the amount of alignment necessary. A similar alignment system is described in U.S. Pat. No. 6,592,825, which is incorporated herein by reference in its entirety. Other types of sensors, as would be apparent to one skilled in the relevant art, may be used in a similar manner to indicate proper alignment of a microfluidic chip in an apparatus of the present invention.

Embodiments of the present invention also include methods for processing a microfluidic chip using an apparatus in accordance with the present invention. For example, one method includes a first step of providing an apparatus, as discussed above that includes at least a chip handling system, a fluid control system, and a detection system, and at least one microfluidic chip, which may be provided in a cartridge or as part of an undiced wafer. Further, a sample material must be loaded onto the microfluidic chip, such as by the use of an optional liquid handling device. Then, the apparatus is programmed to control the flow of the sample material through the microfluidic chip in a predetermined arrangement via the fluid control system, and to detect data from an assay at a predetermined location along a microchannel of the microfluidic chip via the detection system, as discussed above with respect to the figures.

While the invention has been particularly shown and described with reference to preferred embodiments thereof, it will be understood by those skilled in the art that they have been presented by way of example only, and not limitation, and various changes in form and details can be made therein without departing from the spirit and scope of the invention.

Thus, the breadth and scope of the present invention should not be limited by any of the above-described exemplary embodiments, but should be defined only in accordance with the following claims and their equivalents.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

What is claimed is:

1. A microfluidic chip processing apparatus, comprising:
   a housing;
   a microfluidic chip processing area comprising a fluid control system and a detection system, wherein the fluid control system and the detection system are disposed within the housing, the fluid control system having means for providing and controlling forces to move fluids through one or more channels of a microfluidic chip;
   a microfluidic chip storage area spaced apart from the microfluidic chip processing area; and
   a microfluidic chip handling system comprising a conveyor, at least a portion of which extends between the storage area and the processing area, the conveyor having means for engaging a side portion of a microfluidic chip disposed in the storage area, the means for engaging a side portion of a microfluidic chip delivering the microfluidic chip into the housing such that the microfluidic chip is in position to be operably coupled with the fluid control system and the detection system.

2. The apparatus of claim 1, further comprising a liquid handling system having means for dispensing a material into a reservoir disposed on the exterior of the microfluidic chip, the reservoir in fluid communication with a channel disposed within the microfluidic chip.

3. The apparatus of claim 1, further comprising a data output system.

4. The apparatus of claim 3, wherein said data output system is one of a printer, an ethernet connection, floppy disk or CD-ROM drive, a monitor or other visual display device.

5. The apparatus of claim 1, wherein said apparatus has a footprint of approximately the same size as the footprint of a standard 96-well microtiter plate.

6. The apparatus of claim 1 further comprising a plurality of microfluidic chips stacked one upon the other within a cartridge, wherein the microfluidic chip storage area includes a receptacle sized to receive the cartridge.

7. The apparatus of claim 6, wherein the cartridge comprises means for dispensing the plurality of microfluidic chips in series, and wherein the engaging means engage each of the plurality of microfluidic chips in series.

8. The apparatus of claim 7, wherein the cartridge comprises a lift device for biasing the plurality of microfluidic chips upward within the cartridge.

9. The apparatus of claim 8, wherein the lift device comprises a spring.

10. The apparatus of claim 8, wherein the lift device comprises a platform and a piston.

11. The apparatus of claim 1 further comprising a control unit, the control unit including programming for the fluid control system and the detection system.

* * * * *